US008926995B2

(12) United States Patent
Haynes et al.

(10) Patent No.: US 8,926,995 B2
(45) Date of Patent: Jan. 6, 2015

(54) ADJUVANT

(75) Inventors: Barton F. Haynes, Durham, NC (US);
Laurent Verkoczy, Durham, NC (US);
M. Anthony Moody, Durham, NC (US);
Matt T. Holl, Durham, NC (US);
Masayuki Kuraoka, Durham, NC (US);
Garnett Kelsoe, Durham, NC (US)

(73) Assignee: Duke University, Durham, NC (US)

( * ) Notice: Subject to any disclaimer, the term of this patent is extended or adjusted under 35 U.S.C. 154(b) by 21 days.

(21) Appl. No.: 13/989,176

(22) PCT Filed: Nov. 23, 2011

(86) PCT No.: PCT/US2011/062055
§ 371 (c)(1),
(2), (4) Date: May 23, 2013

(87) PCT Pub. No.: WO2012/071521
PCT Pub. Date: May 31, 2012

(65) Prior Publication Data
US 2013/0243850 A1 Sep. 19, 2013

Related U.S. Application Data

(60) Provisional application No. 61/417,130, filed on Nov. 24, 2010.

(51) Int. Cl.
*A61K 39/39* (2006.01)
*A61K 39/21* (2006.01)
*C07K 16/10* (2006.01)
*A61K 39/00* (2006.01)

(52) U.S. Cl.
CPC .............. *A61K 39/39* (2013.01); *C07K 2317/34* (2013.01); *A61K 2039/55516* (2013.01); *A61K 39/21* (2013.01); *A61K 2039/55527* (2013.01); *A61K 2039/55505* (2013.01); *C12N 2740/16134* (2013.01); *C07K 16/1045* (2013.01); *A61K 2039/55522* (2013.01)
USPC .................. 424/278.1; 424/188.1; 424/208.1; 424/450

(58) Field of Classification Search
CPC ..................... C12N 2760/16134; C12N 15/62; C12N 2740/16122; C12N 2740/16022; C12N 2760/16122; C07K 14/4705; C07K 14/70575; C07K 2319/735; C07K 14/005; C07K 14/11; C07K 14/16; C07K 14/435; C07K 14/535; C07K 14/54
See application file for complete search history.

(56) References Cited

U.S. PATENT DOCUMENTS

2002/0052318 A1 5/2002 Haynes et al.

OTHER PUBLICATIONS

He et al. HIV-1 envelope triggers polyclonal Ig class switch recombination through a CD40-independent mechanism involving BAFF and C-Type lectin receptors. The Journal of Immunology 2006, vol. 176, pp. 3931-3941.*
Shen et al. OA021-04. HIV-1 gp41 envelope MPER mutation altered epitope conformation in lipid and increase sensitivity to 2F5 and 4E10 neutralizing antibodies. Abstract for oral presentation published: Oct. 22, 2009, Retrovirology 6 (Suppl 3):O16.*
Ferrari et al. IL-7 enhancement of antigen-driven activation/expansion of HIV-1-specific cytotoxic T lymphocyte precursors (CTLp). Clinical Experimental Immunology 1995, vol. 101, pp. 239-248.*
Ahlers et al. Cytokine, chemokine, and costimulatory molecule modulation to enhance efficacy of HIV vaccines. Current Molecular Medicine 2003, vol. 3, pp. 285-301.*
Moir et al., "B cells in HIV infection and disease", *Nature Reviews Immunology*, 2009, vol. 9, No. 4, pp. 235-245, NIH Public Access Author Manuscript.
Montero et al., "The membrane-proximal external region of the human immunodeficiency virus type 1 envelope: Dominant site of antibody neutralization and target for vaccine design", *Microbiology and Molecular Biology Reviews*, 2008, vol. 72, No. 1, pp. 54-84.
Holl et al., "Stromal cell independent B cell development in vitro: Generation and recovery of autoreactive clones", *Journal of Immunological Methods*, 354, 2010, pp. 53-67.
International Search Report for PCT/US2011/062055, dated Jun. 26, 2012.

* cited by examiner

*Primary Examiner* — Louise Humphrey
(74) *Attorney, Agent, or Firm* — Nixon & Vanderhye P.C.

(57) ABSTRACT

The present invention relates, in general, to human immunodeficiency virus (HIV-1) and, in particular, to a method of enhancing an immune response to an HIV-1 immunogen, and to compounds and compositions suitable for use in such a method.

11 Claims, 11 Drawing Sheets

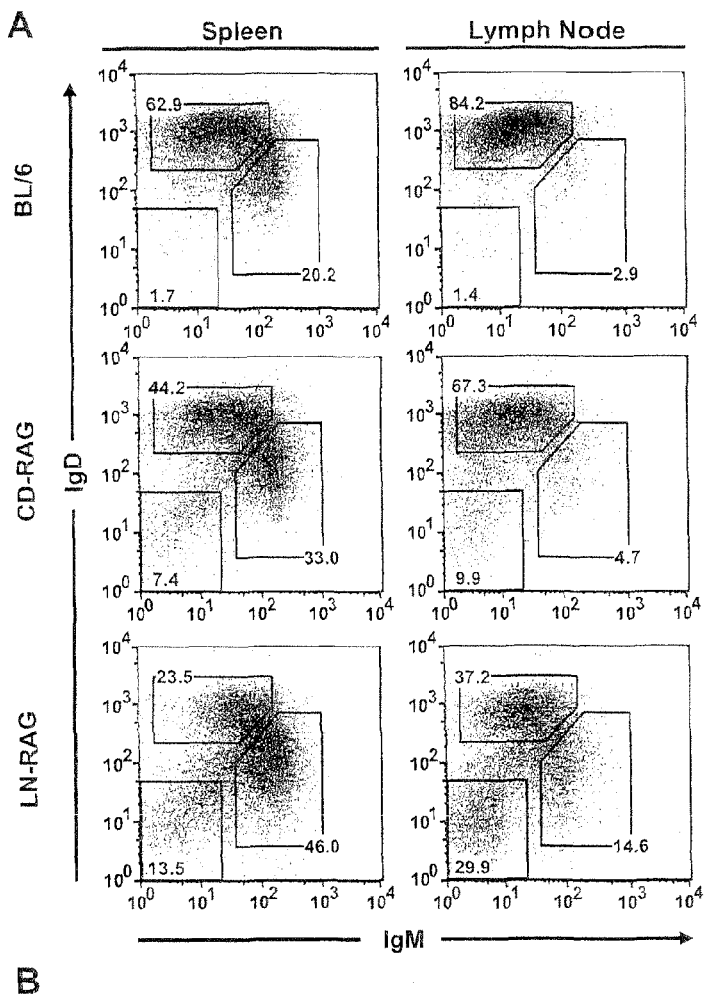
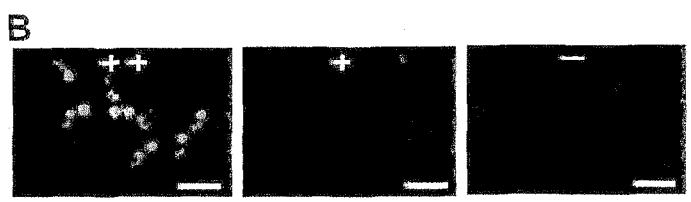
| Sample | N | Serum IgG (mg/ml) | nDNA Ab | | |
|---|---|---|---|---|---|
| | | | (++) | (+) | (-) |
| BL/6 | 5 | 1.42 ± 0.47 | 0 | 1 | 4 |
| CD-RAG | 5 | 1.28 ± 0.47 | 4 | 1 | 0 |
| LN-RAG | 5 | 1.87 ± 0.22 | 1 | 1 | 3 |
Figure 5

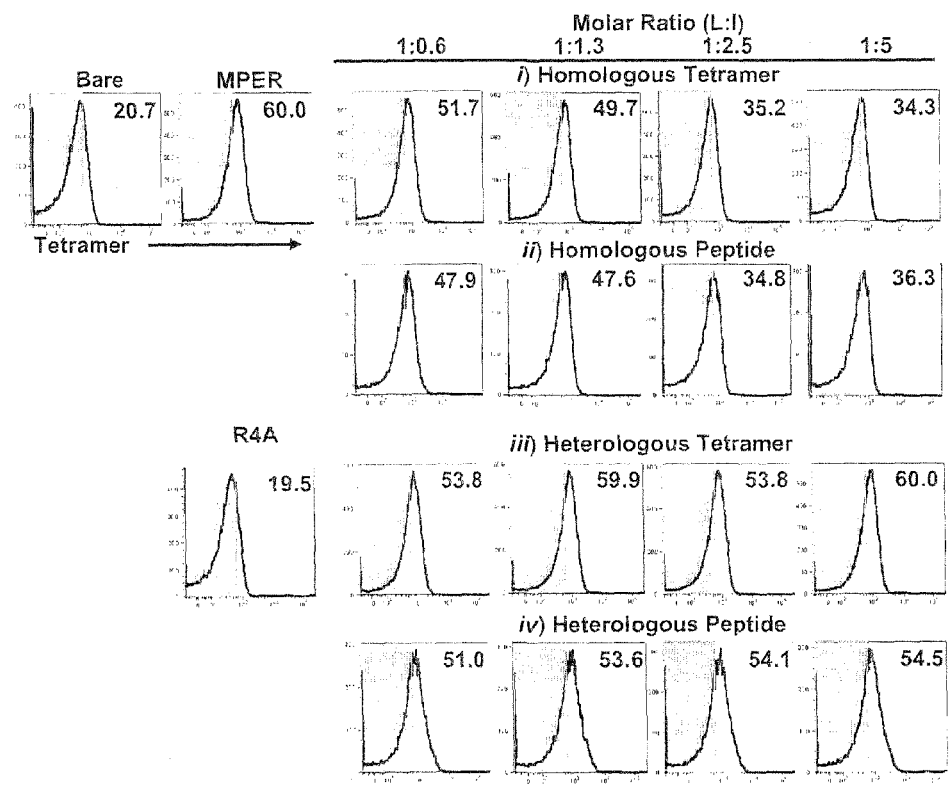

Specific labeling of B-cell lines by MPER tetramer. 13H11 cells (1-1.3 x 10⁶) were incubated in PBS + 3% FCS alone or buffer containing equivalent molar excess amounts of either *i)* unlabeled MPER-tetramer, *ii)* MPER peptide, *iii)* unlabeled R4A tetramer or *iv)* R4A peptide for 30 min. at 0° C. Unlabeled peptide and tetramer concentrations were established to represent 0.6, 1.3, 2.5 and 5.0 M excess of tetramer-associated peptide epitope. Subsequently, cells were labeled with 125 ng of APC-conjugated MPER-tetramer for 30 min. at 0° C. Independent aliquots of 13H11 cells were labeled with APC-conjugated Empty-tetramer as a negative control for peptide-independent binding. 13H11 cells were subsequently analyzed by flow cytometry and the fraction of tetramer binding cells (inset no.) and the M.F.I. of tetramer⁺ cells were determined compared to unlabeled controls. Each histogram is representative of at least 3 independent measurements (n≧3) compiled over 2 independent experiments. All data was acquired using a BD LSRII cytometer and histograms were created using FlowJo software.

Figure 8

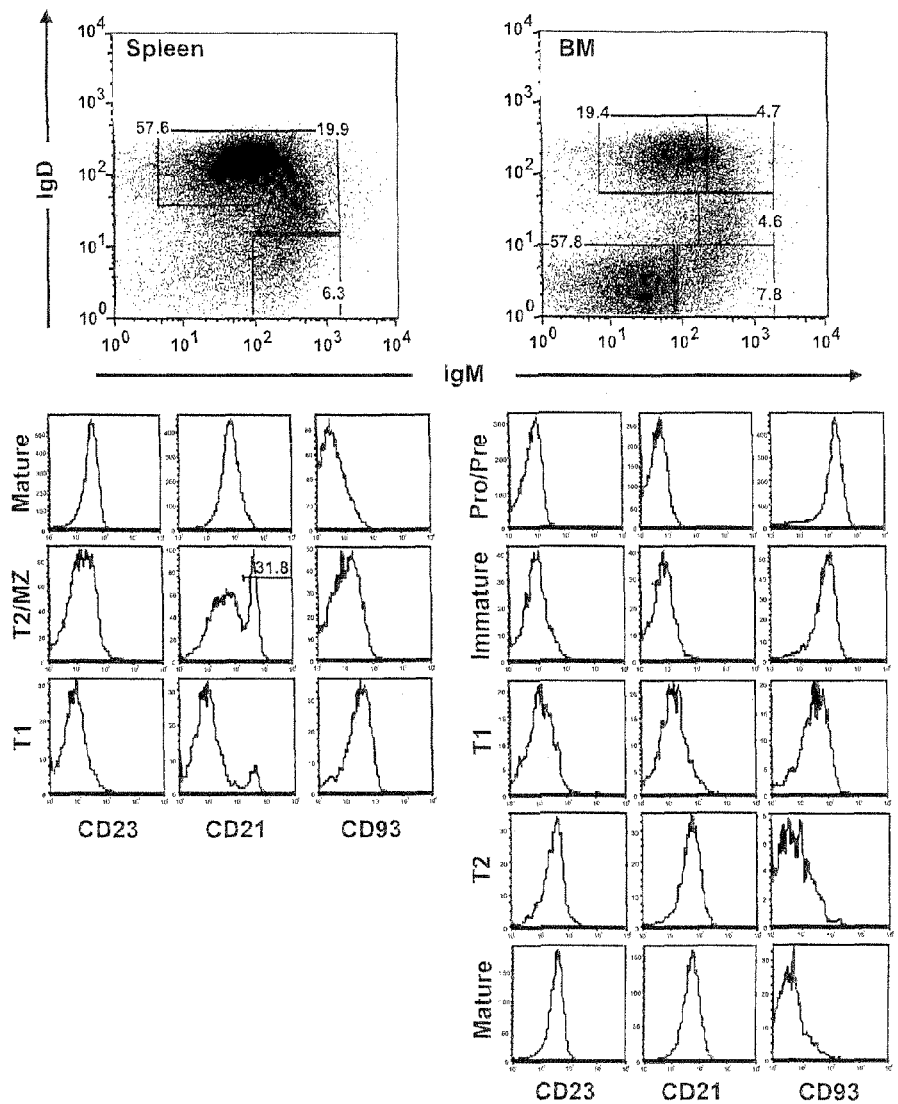

Cell surface markers used to define BM and splenic B-cell populations. BM and spleen cells were harvested from BL/6 mice. Cells ($10^6$) were labeled with mAb to B220, IgM, IgD, CD23, CD21 and CD93. Flow diagrams were gated on live, single B220+ cells. Pre/Pro B (B220$^{int}$IgM$^{neg}$IgD$^{neg}$CD23$^{neg}$CD21$^{neg}$CD93$^{hi}$), Immature B (B220$^{int}$IgM$^{lo}$IgD$^{neg}$CD23$^{neg}$CD21$^{neg}$CD93$^{hi}$), T1 B (B220$^{int}$IgM$^{hi}$IgD$^{lo}$CD23$^{lo}$CD21$^{neg}$CD93$^{hi}$), T2 B (B220$^{hi}$IgM$^{hi}$IgD$^{hi}$CD23$^{hi}$CD21$^{int}$CD93$^{int}$), MZ B cells (B220$^{hi}$IgM$^{hi}$IgD$^{lo}$CD23$^{lo}$CD21$^{hi}$CD93$^{neg}$) and mature B (B220$^{hi}$IgM$^{lo}$IgD$^{hi}$CD23$^{hi}$CD21$^{lo}$CD93$^{neg}$) cells were identified in the BM and/or spleen. Data was acquired using a BD LSRII flow cytometer and analyzed using FlowJo software.

Figure 9

Hybridomas From Culture of 2F5 VH+VL Knock-In Mouse BM With BAFF+ IL-7

Of 154 Mabs:

- 62 did not secrete immunoglobulin i.e. were anergic
- 82 secreted Ig but did not bind MPER
- 10 bound MPER of which...
- 3 neutralized HIV-1

Figure 10B

ADJUVANT

This application is the U.S. national phase of International Application No. PCT/US2011/062055 filed Nov. 23, 2011 which designated the U.S. and claims priority to U.S. Provisional Application No. 61/417,130, filed Nov. 24, 2010, the entire contents of which are incorporated herein by reference.

This invention was made with government support under Grant Nos. AI067854, AI24335 and AI81579 awarded by the National Institutes of Health. The government has certain rights in the invention.

TECHNICAL FIELD

The present invention relates, in general, to human immunodeficiency virus (HIV-1) and, in particular, to a method of enhancing an immune response to an HIV-1 immunogen, and to compounds and compositions suitable for use in such a method.

BACKGROUND

Whereas serum antibody (Ab) responses to HIV-1 envelope antigens are elicited in HIV-infected individuals, the initial Ab response is non-neutralizing and directed to epitopes that are poorly conserved among independent HIV-1 isolates (reviewed in Tomaras and Haynes, Curr. Opin. HIV AIDS 5:373-379 (2009)). Neutralizing Ab responses to HIV-1 do emerge in a significant minority of patients several months after infection (Shen et al, J. Virol. 83:3617-3625 (2009), Wei et al, Nature 422:307-312 (2003)) and select for resistant HIV-1 mutants (Burton et al, Nat. Immunol. 5:233 (2004)).

Among the conserved, neutralizing epitopes of HIV-1 is the membrane proximal external region (MPER) of gp41, a structure critical for viral fusion with target cell membranes (Wyatt and Sodroski, Science 280:1884-1888 (1998)). A series of neutralizing and broadly protective human Abs, 2F5, 4E10, and Z13, react with linear epitopes of the HIV-1 MPER (Muster et al, J. Virol. 67:6642-6647 (1993), Nelson et al, J. Virol. 81:4033-4043 (2007), Zwick et al, J. Virol. 75:10892-10905 (2001)) and yet are rarely elicited by infection (Shen et al, J. Virol. 83:3617-3625 (2009)). Indeed, despite significant effort, no vaccine or immunization strategy has been developed that that routinely induces robust MPER antibody responses (Coeffier et al, Vaccine 19:684-693 (2000), Derby et al, J. Virol. 80:8745-8762 (2006), Eckhart et al, J. Gen. Virol. 77(Pt9):2001-2008 (1996)).

A variety of hypotheses have been proposed to explain ineffective MPER Ab responses to HIV-1 infection and vaccines, including the complexity of HIV epitopes, high frequency of lentivirus mutation, shielding of crucial antigenic determinants by glycosylation, competitive suppression by non-neutralizing surface antigens, and insufficient diversity in the primary Ab repertoire (reviewed in Burton et al, Nat. Immunol. 5:233 (2004)). While each of these conjectures is plausible, the demonstration that the 2F5 and 4E10 MPER Abs avidly react with human and mouse self-antigens, including cardiolipin (Haynes et al, Science 308:1906-1908 (2005), Verkoczy et al, Proc. Natl. Acad. Sci. USA 107:181-186 (2010)), suggested an alternative explanation for the rarity of MPER Ab responses: if HIV-1 MPER neutralizing epitopes mimic host antigens, the normal processes of immunological tolerance could purge sets of MPER specific B cells and impair MPER Ab responses (Haynes et al, Hum. Antibodies 14:59-67 (2005)).

During their development, self-reactive, immature B cells are tolerized by apoptosis, receptor editing, or anergy (Erikson et al, Nature 349:331-334 (1991), Gay et al, J. Exp. Med. 177:999-1008 (1993), Hartley et al, Cell 72:325-335 (1993), Hartley et al, Nature 353:765-769 (1991), Nemazee and Burki, Nature 337:562-566 (1989), Tiegs et al, J. Exp. Med. 177:1009-1020 (1993)). Self-reactive B cells that are not purged in the bone marrow (BM) can remain susceptible to mechanisms of peripheral tolerance mechanisms that limit their capacity to respond to antigen ligands (Adams et al, Proc. Natl. Acad. Sci. USA 87:5687-5691 (1990)). Therefore, the fate of self-/HIV-reactive B cells should be investigated to determine whether: i) these cells are purged from the mature B-cell repertoire during their development in BM or ii) these cells are present in peripheral lymphoid tissues but held in an anergic state. This information is vital to the logical design of future vaccines that attempt to elicit Ab responses to the MPER of HIV.

The influence of tolerance on MPER-reactive B-cell development has recently been investigated by the generation of 2F5 VDJ "knock-in" (2F5 VDJ-KI) mice (Verkoczy et al, Proc. Natl. Acad. Sci. USA 107:181-186 (2010)). B-cell development in 2F5 VDJ-KI mice is blocked in the BM at the transition of small pre-B to immature B cells (Verkoczy et al, Proc. Natl. Acad. Sci. USA 107:181-186 (2010)). This developmental blockade is virtually identical to that observed in mice expressing B cell receptors (BCRs) for MHC (Nemazee and Burki, Nature 337:562-566 (1989)) or double-stranded DNA (Chen et al, Immunity 3:747-755 (1995)). Unlike the studies that utilize BCRs with known specificity to self-antigens (MHC and DNA), the self-antigen(s) that mediates the selection of 2F5 VDJ-KI B cell development has not yet been identified. Therefore, it is not clear whether this induction of tolerance in MPER-reactive B cells is mediated by interaction with cellular lipids or polypeptide antigens, as both 2F5 and 4E10 mAbs show significant but independent binding to each class of antigen (Alam et al, Proc. Natl. Acad. Sci. USA 105:20234-20239 (2009), Ofek et al, J. Virol. 84:2955-2962 (2010)).

Structural analyses of 2F5 and 4E10 mAbs indicate that their capacity to react with lipid antigens is potentiated by extended, hydrophobic HCDR3 motifs that have minimal interactions with the nominal MPER polypeptide (Alam et al, Proc. Natl. Acad. Sci. USA 105:20234-20239 (2009), Cardoso et al, Immunity 22:163-173 (2005), Ofek et al, J. Virol. 78:10724-10737 (2004)). Reciprocally, select mutations in the HCDR3 of 2F5 and 4E10 impair MPER polypeptide binding with little effect on lipid reactivity (Alam et al, Proc. Natl. Acad. Sci. USA 105:20234-20239 (2009)). Moreover, mutations of the 41-reactive and/or lipid-binding hydrophobic loop of HCDR3 regions will significantly reduce the ability of 2F5 and 4E10 to neutralize HIV infection (Alam et al, Proc. Natl. Acad. Sci. USA 105:20234-20239 (2009), Ofek et al, J. Virol. 84:2955-2962 (2010)), Scherer et al, Proc. Natl. Acad. Sci. USA 107:1529-1534 (2010)). These data suggest that removal of B cells that express Ab with either lipid-reactivity or the appropriate MPER peptide specificity would result in the loss of HIV neutralizing activity.

Without resorting to transgenic or "knock-in" mice, it is possible to identify specific B cells either by antigen-binding (Lalor et al, Eur. J. Immunol. 22:3001-3011 (1992), McHeyzer-Williams et al, J. Exp. Med. 178:295-307 (1993), McHeyzer-Williams et al, Nature 350:502-505 (1991)) or by anti-idiotypic mAb (Reth et al, Eur. J. Immunol. 9:1004-1013 (1979), Takemori et al, Eur. J. Immunol. 12:1040-1046 (1982)). The development of B-cell tetramers, analogous to those routinely used to identify antigen-specific T cells (Altman et al, Science 274:94-96 (1996)), has greatly enhanced the ability to identify and isolate antigen-specific B cells despite their low frequencies (Newman et al, J. Immunol. Methods 272:177-187 (2003)). B-cell tetramers have been used to identify MPER peptide-reactive B cells within central and peripheral lymphoid tissues and to follow the fates of tetramer-binding cells in vivo. These B-cell tetramer reagents have been used to test the prediction that HIV gp41 MPER-reactive cells should be enriched in developmentally immature B-cell compartments but rare or absent in mature B-cell populations.

A BM culture system has been described that supports the survival, proliferation and differentiation of virtually all B2-lineage developmental stages (Holl et al, J. Immunol. Methods 354:53-67 (2010)). These culture-derived (CD) B-lineage cells are phenotypically and functionally similar to their in vivo counterparts (Holl et al, J. Immunol. Methods 354:53-67 (2010)) but develop in the absence of many self antigens and absent the environment of the BM (Sandel et al, J. Immunol. 166:5935-5944 (2001), Sandel and Monroe Immunity 10:289-299 (1999)). CD B cells are enriched for autoreactive specificities, and maintain this bias even after transfer to RAG1 deficient hosts (Holl et al, J. Immunol. Methods 354:53-67 (2010)). A determination has now been made as to whether B cells specific for the 2F5 peptide epitope of MPER, independent of association with lipids, are tolerized. Importantly, these cultures contain MPER-reactive B cells and mice reconstituted with CD B cells generated both robust germinal center (GC) responses and serum IgG Ab upon immunization with HIV peptide. In contrast, C57BL/6 animals did not respond to MPER immunization because these MPER-reactive B-cell subsets were lost beyond the BM transitional B cell stages in vivo.

Thus, the present invention results, at least in part, from studies demonstrating that MPER-reactive B cells are generated but are subsequently lost during T1 and T2 stages of B-cell development in the BM. The invention provides an adjuvant that breaks peripheral tolerance/anergy so that broadly neutralizing antibodies can be induced.

SUMMARY OF THE INVENTION

In general, the present invention relates to HIV-1. More specifically, the invention relates to a method of enhancing an immune response to an HIV-1 immunogen and to compounds and compositions suitable for use in such a method.

Objects and advantages of the present invention will be clear from the description that follows.

BRIEF DESCRIPTION OF THE DRAWINGS

(FIG. 1A) NIH-3T3 cells were labeled with 2F5 mAb and bound Ab was detected using anti-human IgG-FITC. Scale bar equals 20 µm for all images. Images were acquired using a Zeiss Axiovert 200M confocal immunofluorescent microscope at 200× magnification. 13H11 cells (1-1.3×10$^6$) were incubated in PBS+3% FCS containing equivalent molar excess amounts of either unlabeled SP62 (MPER) peptide (○), unlabeled MPER-tetramer (●) or control unlabeled R4A peptide (Δ) and unlabeled R4A tetramer (▲) for 30 min at 0° C. Unlabeled peptide and tetramer concentrations were established to represent 0.6, 1.3, 2.5 and 5.0 M excess of labeled tetramer-associated peptide epitope. Subsequently, cells were labeled (L) with 125 ng of allophycocyanin (APC)-conjugated MPER-tetramer for 30 min at 0° C. Other 13H11 cells were labeled with either APC-conjugated Empty-tetramer (short dashed line) or R4A-tetramer (long dashed line) as negative controls for binding. Also, P3 (◇) cells were labeled with APC-conjugated MPER-tetramer as a negative control for binding. Cells were analyzed by FACS and (FIG. 1B) fraction of tetramer-binding cells and (FIG. 1C) M.F.I. of tetramer$^+$ cells was determined. Each data point represents the average of at least 3 independent measurements (n≥3) compiled over 2 independent experiments. (FIG. 1D) BL/6 BM cells (10$^6$) were incubated alone or with 10-fold molar excess of MPER peptide. Then, BM cells were incubated alone or labeled with 125 ng of APC-conjugated MPER-tetramer. All samples were washed and labeled with mAb to B220. FACS plots are pre-gated on live, single, B220$^+$ cells. Data presented are representative of 2 independent experiments.

(FIG. 4A) Cells were labeled with 125 ng of MPER-APC (♦), R4A-APC (●) or Empty-APC (▲) tetramer. Cells were washed and labeled with mAb to B220, IgM and IgD. Tetramer binding was assessed on each population using a BD LSRII flow cytometer. Plots are pre-gated on live, single B220$^+$ cells. Analysis of specific B-cell subsets was performed using surface staining criteria previously described (Ueda et al, J. Immunol. 178:3593-3601 (2007)). Each data point represents the average and S.E.M. of multiple independent measurements (♦; n=14, ●; n=10, ▲; n=7) for each population compiled over 3-4 independent experiments. Significant differences (*; p<0.05) between groups were determined by (two-tailed) Student's t-test. (FIG. 4B) BM cells were cultured to generate Ig$^+$ B cells (Boll et al, J. Immunol. Methods 354:53-67 (2010)). Cells were labeled with 125 ng/10$^6$cells of MPER-APC tetramer and with mAb to B220. Live MPER-tetramer$^+$B220$^+$ cells were sorted using BD FACSVantage flow cytometer. Unselected and selected (MPER$^+$B220$^+$) cells were stimulated using 5 µg/ml LPS and 20 ng/ml BAFF for 72 h. Cells were harvested, washed and 1.5-2×10$^3$ cells were incubated for 4 h on ELISpot plates coated with goat anti-mouse Ig(H+L) capture reagent. Membranes were probed with either 20 μM biotin-MPER or biotin-R4A peptide to determine the frequency and enrichment of MPER peptide-specific cells. ELISpot images are representative of 2 independent experiments performed in duplicate.

FIGS. 5A-5C. RAG-1$^{-/-}$ mice reconstituted with CD B cells, but not lymph node (LN) B cells, results in serum autoantibody. Non-adherent BL/6 BM cells were cultured to generate CD B cells for injection into B6.RAG$^{-/-}$ mice as previously described (Holl et al, J. Immunol. Methods 354: 53-67 (2010)). BL/6 LN cells were isolated for transfer into B6.RAG$^{-/-}$ mice (LN-RAG). (FIG. 5A) At 6 wk post-transfer, spleen and LN cells from BL/6 (top), CD-RAG (RAG-deficient mice reconstituted with CD B cells) (middle) or LN-RAG (RAG-deficient mice reconstituted with LN cells) (bottom) mice were labeled with mAbs to B220, IgM, IgD, CD93 and CD21. Flow diagrams were pre-gated on live, single, B220$^+$ cells and were representative of each mouse analyzed (n=5 per group). Sera from each experimental group were collected via retro-orbital eye bleeding at 6 wk post-transfer. (FIG. 5B) Sera samples were diluted (1:160) and used to labeled C. luciliae substrate slides. After overnight washing, Ab bound to cells was detected using rat anti-mouse IgG-FITC Ab. All images were acquired using a Zeiss Axiovert 200M confocal immunofluorescent microscope with an exposure time of 300 ms at 400× magnification. Representative examples of strong (++), weak (+) and no (−) nDNA binding activity are presented. Scale bar equals 20 μm for all images. (FIG. 5C) Concentrations of serum IgG were determined using anti-mouse IgG-specific ELISAs including standard curves. Each sera sample (1:160 dil) was screened for reactivity to nDNA by immunofluorescent microscopy with a fixed exposure time (300 ms) at 400× magnification. Each group contained multiple mice (n=5) that were screened independently.

(FIG. 6A) MLN and (FIG. 6B) spleen cells were harvested at d16 after 1-2 immunizations. Cells were labeled with mAb to B220, IgM, IgD, TCRβ and GL-7. The percent of B220$^{hi}$GL-7$^{hi}$ B cells of total B220$^{hi}$ cells was determined by flow cytometry. Each group contained multiple mice (n=6-12) compiled over multiple (n=2-4) independent experiments. Significant differences (*; p≤0.05 and **; p≤0.01) between groups were determined by (two-tailed) Student's t-test. 5 μm sections of spleen from BL/6 and CD-RAG mice at d16 after (FIG. 6C) primary or (FIG. 6D) secondary immunizations were labeled with mAbs to B220-AF350 (blue), TCRβ-PE (red) and GL-7-FITC (green). FITC signal was amplified using anti-FITC-AF488 Ab. Scale bar equals 50 μm for all images. Images were acquired using a Zeiss Axiovert 200M confocal immunofluorescent microscope at 200× magnification.

(FIG. 7A) BL/6 (n=5) and CD-RAG (n=5) mice were immunized (ip) with 10 μg (4-hydroxy-3-nitrophenyl)acetyl (NP)$_{13}$-chicken gamma globulin (CGG) in alum. Serum was harvested at day 12 post-immunization. ELISA plates were coated with either (4 hydroxy-5-iodo-3 nitrophenyl)acetyl (NIP)$_{19-25}$-bovine serum albumin (BSA) or NIP$_5$-BSA capture antigens. NIP-specific Ab was detected using goat anti-mouse IgG Ab. Purified H33Lγ1 (IgG) mAb was used as a standard curve to calculate antigen-specific serum Ab concentration. These results are from 2 independent experiments. (FIG. 7B) BL/6 (n=12-15) and CD-RAG (n=17-20) mice were immunized (ip) 1-2 times with 10 μg MPER peptide in alum. Serum was harvested at d16 post-immunization. ELISA plates were coated with MPER-specific capture antigen and bound Ab was identified using a goat anti-mouse IgG detection reagent. Purified 13H11 mAb was used as a standard curve to calculate antigen-specific serum Ab concentration. These results are pooled from 3-4 independent experiments. Significant differences (*; p<0.05, **; p<0.01) between groups were determined by (two-tailed) Student's t-test.

FIG. 8. Representative FACS histograms demonstrating MPER-tetramer specificity.

FIG. 9. FACS plots describing B-cell population identification scheme.

FIGS. 10A and 10B. Hybridomas from culture of 2F5 VH and VL knock-in mouse BM with BAFF and IL-7.

DETAILED DESCRIPTION OF THE INVENTION

Figure 1:
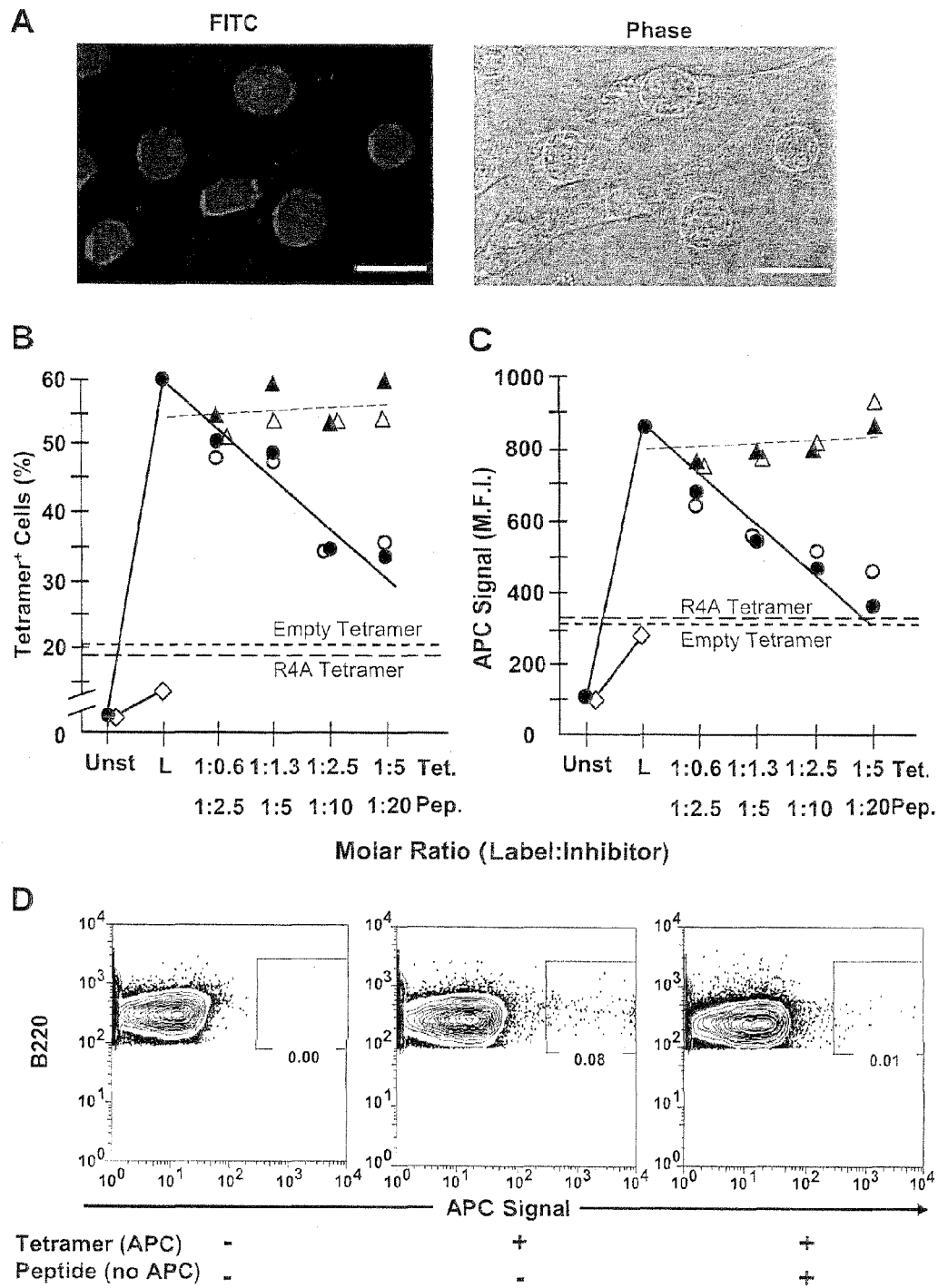
FIGS. 1A-1D. Labeling by MPER-tetramer is blocked by homologous (MPER) but not heterologous (R4A) reagents.

The present invention relates generally to a method of inducing the production in a subject (e.g., a human subject) of broadly neutralizing antibodies against HIV-1. The invention includes an adjuvant suitable for use in combination with an HIV-1 vaccine, which adjuvant breaks peripheral tolerance/anergy so that broadly neutralizing anti-HIV-1 antibodies are produced. The adjuvant comprises BAFF and IL-7. In accordance with the invention, an HIV-1 immunogen, BAFF and IL-7 are administered to the subject in an amount and under conditions such that naïve B cells or their B cell intermediate clones are produced that secrete broadly neutralizing anti-HIV-1 antibodies.

HIV-1 antigens suitable for use in the invention include membrane-proximal external region (MPER) antigens (Armbruster et al, J. Antimicrob. Chemother. 54:915-920 (2004), Stiegler and Katinger, J. Antimicrob. Chemother. 512:757-759 (2003), Zwick et al, Journal of Virology 79:1252-1261 (2005), Purtscher et al, AIDS 10:587 (1996)) and variants thereof, for example, variants that confer higher neutralization sensitivity to MPER Mabs 2F5 and 4E10 or to other broadly neutralizing Envs, such as the MPER mutant Env peptide lipid complex containing a L669S mutation in the MPER (Shen et al, J. Virology 83:3617-25 (2009)). Suitable immunogens include those shown in FIGS. 25 and 26, as well as FIGS. 16B, 16C, FIG. 17, FIG. 18 and FIG. 20 of U.S. Prov Appln. No. 61/282,526. In one preferred embodiment, the variant is a MPER epitope peptide with an L669S mutation that confers higher neutralization sensitivity to MPER mAbs 2F5 and 4E10 (Shen et al, J. Virology 83: 3617-25 (2009)).

HIV-1 antigens suitable for use as immunogens in accordance with the invention also include transmitted founder HIV-1 Envs, or fragments thereof. These fragments can be representative of portions of the CD4 binding site of gp120 (Chen et al, Science 362(5956):1123-7 (2009)), MPER sequences, portions of gp120 incorporating the V2, V3 regions of gp120 (Walker et al, Science 326(5950):285-9 (2009) Epub 2009 Sep. 3), etc (e.g., see the sequences for 1086, 089, 6240, 040_C9 and 63521 set forth in FIGS. 27 and 28 of U.S. Prov Appln. No. 61/282,526). Preferred Env antigens include the Malawi 1086 clade C, 6321 and the US clade B 040_C9 gp140 oligomers (see FIGS. 17 and 18 of U.S. Prov Appln. No. 61/282,526) (Keele et al, Proc. Natl. Acad. Sci. USA 105:7552-7 (2008)) produced as previously described (Liao et al, Virology 30:268-282 (2006)), which have induced in guinea pigs considerable breadth in neutralizing antibodies (see FIG. 19A of U.S. Prov Appln. No. 61/282,526), mixed with the clade B JRFL gp140 Env, or fragment thereof, that selectively expresses the MPER neutralizing epitopes (see FIG. 28 of U.S. Prov Appln. No. 61/282,526). The JRFL gp140 Env oligomer (see FIGS. 19B, 20, 21A and 21B of U.S. Prov Appln. No. 61/282,526) constitutively binds the 2F5 mAb. The JRFL oligomer deglycosylated using 500 U of PNgase endoglycosidase (New England BioLabs, Ipswich, Mass.) has enhanced binding of 2F5 and new binding of the 4E10 mAb (exposure of the 4E10 epitope on gp41) (see FIGS. 21A and 21B of U.S. Prov Appln. No. 61/282,526). The enhanced binding of 4E10 to deglycosylated JRFL is also shown in surface plasmon reasonance (SPR) analysis in FIG. 22 of U.S. Prov Appln. No. 61/282,526.

It will be appreciated from the foregoing that suitable immunogens include, for example, 63521.B, 6240.B, 1086.C, 089.C, 040.B transmitted founder recombinant gp140s or gp120s, the MPER 656 peptide, liposome complexes, the gp41 inter liposome complexes, the deglycosylated JRFR gp140 env and other envs or the recombinant enzyme kynureninase that includes the ELDKWAS sequence. (See, for example, PCT/US2010/002770, PCT/US2010/01017 and PCT/US2010/01018.)

Centralized (e.g., consensus, ancestral or center of the tree) sequences can also be used as the HIV-1 immunogen (see, for example, PCT/US04/30397), as can mosaic proteins (see, for example, PCT/US06/32907).

The BAFF plus IL-7 adjuvant can be co-administered with the HIV-1 immunogen (vaccine) or it can be administered shortly before (e.g., about 1-14 days, preferably, 1-7 days, more preferably, 1-4 days) administration of the immunogen. Administration shortly after immunization can be effective under certain circumstances. Optimum regimens can be determined by one skilled in the art and can vary with, for example, the immunogen, the patient and the specific effect sought. BAFF and IL-7 can be administered together or separately (e.g., with IL-7 being administered first). DNA sequences encoding the adjuvant components can also be administered (e.g., at a dose of from about 1 mg to about 5 mg of DNA of each, advantageously, administered, e.g., IM or SC.) If expressed in a vector, for example, BCG or rAd, the dose can be, for example, about $10^8$ colonies of BCG or about $10^{10}$ pfu of rAd.

In accordance with the invention, the HIV-1 antigen can be present in a liposome with BAFF and/or IL-7 (e.g., about 20 to 200 U of BAFF and IL-7 incorporated in the liposome). Liposomes expressing MPER antigens (Dennison, et al, J. Virology 83:10211-23 (2009)) with or without Toll Like Receptor (TLR) agonists have been described (see, for example, WO 2008/127651). Gp41 intermediate state protein has been described by Frey et al (Proc. Natl. Acad. Sci. USA 105-3739-44 (2008)). The gp41 intermediates can be formulated with liposomes (see FIGS. 24A and 24B of U.S. Prov Appln. No. 61/282,526) to form a stable immunogens that bind well to 2F5 and 4E10 (see FIG. 25 of U.S. Prov Appln. No. 61/282,526).

Liposomes suitable for use in the invention include, but are not limited to, those comprising POPC, POPE, DMPA (or sphingomyelin (SM)), lysophosphorylcholine, phosphatidylserine, and cholesterol (Ch). While optimum ratios can be determined by one skilled in the art, examples include POPC: POPE (or POPS):SM:Ch or POPC:POPE (or POPS):DMPA: Ch at ratios of 45:25:20:10. Alternative formulations of liposomes that can be used include DMPC (1,2-dimyristoyl-sn-glycero-3-phosphocholine) (or lysophosphorylcholine), cholesterol (Ch) and DMPG (1,2-dimyristoyl-sn-glycero-3-phoshpho-rac-(1-glycerol) formulated at a molar ratio of 9:7.5:1 (Wassef et al, ImmunoMethods 4:217-222 (1994); Alving et al, G. Gregoriadis (ed.), Liposome technology $2^{nd}$ ed., vol. III CRC Press, Inc., Boca Raton, Fla. (1993); Richards et al, Infect. Immun. 66(6):285902865 (1998)). The above-described lipid compositions can be complexed with lipid A and used as an immunogen to induce antibody responses against phospholipids (Schuster et al, J. Immunol. 122:900-905 (1979)). A preferred formulation comprises POPC:POPS:Ch at ratios of 60:30:10 complexed with lipid A according to Schuster et al, J. Immunol. 122:900-905 (1979). The optimum ratio of immunogen to adjuvant to total lipid can vary, for example, with o the immunogen and the liposome.

DNA sequences encoding HIV-1 immunogens can be administered to a subject under conditions such that the immunogen is produced in vivo. When a DNA prime or boost is used, suitable formulations include a DNA prime and a recombinant adenovirus boost and a DNA prime and a recombinant mycobacteria boost, where the DNA or the vectors encode at least one HIV-1 immunogen.

A variety of additional adjuvants can also be used in the present invention, such as squalene-based adjuvants (Kaldova, Biochem. Biophys. Res. Communication, Dec. 16, 2009 E-pub ahead of print) and/or TLR agonists (e.g., a TRL 3, TRL 5, TRL4, TRL9 or TRL7/8 agonist, or combination thereof) that facilitate robust antibody responses (Rao et al, Immunobiol. Cell Biol. 82(5):523 (2004)). Other adjuvants that can be used include alum and Q521. Oligo CpGs in an oil emulsion such as Emulsigen (an oil in water emulsion) (Tran et al, Clin. Immunol. 109(3):278-287 (2003)) can also be used. Additional suitable adjuvants include those described in. U.S. application Ser. No. 11/302,505, filed Dec. 14, 2005, including the TRL agonists disclosed therein. (See also Tran et al, Clin. Immunol. 109:278-287 (2003), US Appln Nos. 20030181406, 20040006242, 20040006032, 20040092472, 20040067905, 20040053880, 20040152649, 20040171086, 20040198680, 200500059619).

Liposomes loaded as described above are examples of immunogens that can be used to overcome peripheral deletion and/or anergy of B cells that do get driven to make polyreactive neutralizing antibodies.

The mode of administration of the HIV-1 immunogen, or encoding sequence, and adjuvant can vary with, for example, the immunogen, the patient and the effect sought, similarly, the dose administered. Typically, the administration route will be intramuscular, intravenous, intraperitoneal or subcutaneous injection. Additionally, the formulations can be administered via the intranasal route, or intrarectally or vaginally as a suppository-like vehicle. Optimum dosing regimens can be readily determined by one skilled in the art (immunization via intramuscular injection being preferred). The immunogens are preferred for use prophylactically, however, their administration to infected individuals may reduce viral load.

Certain aspects of the invention are described in greater detail in the non-limiting Examples that follow.

EXAMPLE 1

Experimental Details

Mice. C57-BL/6 and Rag1$^{-/-}$ (B6.129S7-RagItmIMom/J) mice were obtained from Jackson Laboratory (Bar Harbor, Me.). 2F5 VH-KI mice were provided by Dr. Verkoczy. CD-RAG mice were created by tail vein injection of CD cells into Rag1$^{-/-}$ mice as previously described (Holl et al, J. Immunol. Methods 354:53-67 (2010)). LN-RAG mice were created by tail vein injection of 2×10$^7$ cells isolated from BL/6 LN. Mice were housed in a pathogen-free barrier facility and were used at 6-8 wk of age. These studies were approved by the Duke University Animal Care and Use Committee.

Antibodies and FACS. To identify, characterize, and isolate lymphocytes, mAbs included: B220-PacificBlue (RA3-6B2), CD23-biotin (B3B4), CD93-APC (AA4.1), GL7-FITC (GL7) and APC-Alexa750-conjugated streptavidin were purchased from BD Pharmingen (San Diego, Calif.); and anti-mouse IgM-PEcy7 (eB121-15F9), anti-mouse IgD-FITC (11-26), CD21-PE (eBio8D9) and TCRβ-APC (H57-597) were purchased from eBioscience (San Diego, Calif.). Single cell suspension of dissociated tissues and cultured cells were counted on a hemacytometer using Trypan Blue exclusion to determine total cell numbers. $10^6$ cells were suspended in FACS Buffer and labeled with mAbs described above. FACS buffer contained 1×PBS (pH7.2) with 3% FBS (Sigma) and 0.01% Sodium Azide. Propidium iodide (PI) was used to exclude dead cells from the samples. All FACS analysis was performed using a BD LSRII or Canto cytometer and presented with FlowJo software. Cell sorting was performed on a BD FACSVantage cytometer.

Peptides and Tetramers. All peptides were synthesized by SynPep Corporation (Dublin, Calif.). All tetramers were created as previously described (Verkoczy et al, PLoS One 4:37215 (2009)). Peptides used for immunization, ELISA, tetramer and ELISpot analysis include: DP178-Q16L— YTSLIHSLIEESQNQLEKNEQELLELDKWASLWNWF, SP62 (MPER)—GGGQQEKNEQELLELDKWASLWN, R4A—GGGGGDWEYSVWLSN. All tetramer reagents used for FACS were labeled with APC to track antigen-specific B-cell populations. Empty-tetramer reagent was biotin-saturated streptavidin-APC that did not contain peptide. All tetramer reagents were used at ~10 nM concentration (~125 ng per $10^6$ cells) to label cells for 30 mins on ice. Cells were then washed and labeled with mAbs (described above) to determine specific B-cell populations.

Cell lines. P3 and 13H11 cell lines were grown and maintained in DMEM media (Gibco) containing 10% FCS, $10^{-4}$M 2-ME and penicillin/streptomycin (P/S) antibiotics. R4A cell line was grown and maintained in DMEM media (Gibco) containing 20% FCS, 1% MEM non-essential amino acids, $10^{-4}$M 2-ME and P/S antibiotics as previously described (Shefner et al, J. Exp. Med. 173:287-296 (1991)).

B-cell culture system. BM cells were cultured to generate CD B cells as previously described (Holl et al, J. Immunol. Methods 354:53-67 (2010)). Briefly, mice were sacrificed by cervical dislocation and BM was collected from long bones of the hind legs by flushing with cold, serum-containing media. BM was plated for 5-10 mins in a humidified $CO_2$ incubator at 37° C. to remove adherent cell populations, Non-adherent cells were collected and centrifuged at ~400×g at 4° C. for 5 mins. RBCs were lysed using 1×ACK buffer. Cells were washed and the number of live cells was determined using hemacytometer and Trypan Blue exclusion. BM cells were plated at $7.5\times10^5$ cells/ml (25 mls) in T-75 flasks for 4 d in IMDM (Gibco) containing $10^{-4}$ M 2-ME, 10% HyClone Serum (Defined) and P/S antibiotics. Recombinant cytokines were added at 10 ng/ml IL-7 or 20 ng/ml BAFF from R&D Systems (Minneapolis, Minn.).

ELISA. ELISA plates (BD Falcon) were coated (overnight, 4° C.) with 2-5 µg/ml (50 µl/well) of capture reagent (NIP-BSA or DP178-Q16L) in carbonate buffer (0.1M; pH9.5). Coated plates were washed with 1×PBS (pH7.4) containing 0.1% Tween-20 and 0.5% BSA (USB Corporation). Wells were incubated (2 hrs; 25° C.) with blocking buffer (PBS (pH7.4), 0.5l% BSA, 0.1% Tween-20). Serum samples were initially diluted from 1:5 to 1:50; followed by serial 3-fold dilutions. Purified mouse IgG (H33Lγ1 and 13H11) mAbs were used as a standard (10-30 µg/ml to 1.5-5 ng/ml) to determine serum Ab concentrations. HRP-conjugated goat anti-mouse IgG was used to detect bound antibody (Southern Biotechnology Associates, Birmingham, Ala.). Only samples that fell within the linear portion of the standard curve were used for analysis.

ELISpot assays. ELISpot plates (Millipore) were coated with 2 µg/ml (50 µl/well) of goat anti-mouse Ig(H+L) in 0.1M Carbonate Buffer (pH9.5) overnight at 4° C. Washing/Blocking buffer contained 1×PBS (pH7.4), 0.1% Tween-20 and 0.5% BSA (USB Corporation). Antigen-specific AFC: LPS-activated B cells were washed and plated at $1.5-2\times10^3$ cells/well in triplicate. Cells were incubated at 37° C. in a humidified $CO_2$ incubator for 4 h with IMDM media described above. Plates were washed and re-blocked for 1-2 d using blocking buffer described above. Membranes were probed with 20 µM biotin-DP178-Q16L or biotin-R4A peptide for 2 h at room temperature. Streptavidin-AP (Southern Biotech) and SIGMA FAST BCIP/NBT (Sigma) were used to develop spots. Pictures were taken using a Canon EOS 20D digital camera with an EFS60 mm lens attached. Total AFC: LPS-activated B cells were washed and plated at $2.5-5\times10^2$ cells/well in triplicate. Plates were washed and re-blocked as described above. Membranes were probed with goat-anti-mouse IgM-AP and IgG-AP detection Ab. SIGMA FAST BCIP/NBT (Sigma) was used to develop spots.

Immunizations. NP-CGG immunizations: 6-8 wk old BL/6 mice were immunized (ip) with $NP_{13}$-CGG (5 µg) precipitated in alum and suspended in 200 µl PBS. CD-RAG mice were immunized with equivalent amounts of antigen 3.5 wk after CD B cell transfer. Mice were bled before and 12 d after immunizations to determine antigen-specific serum Ab levels. MPER immunizations: 6-8 wk old BL/6 mice were immunized (ip) 1-2 times with DP178-Q16L peptide (10 µg) precipitated in alum and suspended in 200 µl PBS. CD-RAG mice were immunized (ip) 1-2 times with DP178-Q16L peptide (10 µg) precipitated in alum and suspended in 200 µl PBS 3.5-4 wk after CD B-cell transfer. Mice were bled as indicated to determine antigen-specific serum Ab levels. Spleen and MLN were harvested 16 d post-immunization and analyzed via FACS and immunofluorescent labeling of tissue sections.

Immunofluorescence Assays Histology A portion of the spleen and individual mesenteric lymph node (MLN) from naïve and immunized mice were embedded in OCT compound and snap frozen using $N_2$-chilled 2-methylbutane and stored at −80° C. 5 µm sections were prepared using a cryostat and poly-lysine coated slides. Sections were fixed with 1:1 Acetone:Methanol for 10 min at −20° C. and labeled with B220-biotin, TCRβ-PE (red) and GL-7-FITC (green) mAb. FITC signal was amplified using anti-FITC-AF488 mAb (Invitrogen). Streptavidin-AlexaFluor350 (Invitrogen) was used to amplify B220-biotin signal (blue). Images were acquired using a Zeiss Axiovert 200M confocal immunofluorescent microscope. Crithidia luciliae Slides containing C. luciliae (Scimedx Corporation, Denville, N.J.) were rehydrated (PBS (pH7.4); 30 min; 25° C.). Samples were blocked (2 hr; 25° C.) using PBS (pH7.2) containing rat anti-mouse CD16/CD32 (1%), purified rat IgG (5%) and Tween-20 (0.1%). Samples were washed (1 min) in PBS (pH7.2) containing BSA (1%) and Tween-20 (0.1%). Samples were labeled with serum (1:160) (2 hrs; 25° C.) followed by extensive washing (2×250 mls; 10 min each; 1×250 mls; overnight). Ab was detected using goat anti-mouse IgG-FITC Ab (2 hrs; 25° C.) followed by extensive washing (3×150 mls; 10 min each). Coverslips were mounted to slides using Fluoromount-G (Southern Biotechnology Associates, Birmingham, Ala.). Images were acquired using a Zeiss Axiovert 200M confocal immunofluorescent microscope (400× magnification, 300 ms exposure). NIH-3T3 cells For detection of 2F5 mAb reactivity with mouse cellular antigens, NIH-3T3 cells (1-2×10⁴ cells/ml; 10 mls) were plated onto 10 cm tissue culture plates (24 hrs; 37° C.) containing sterile glass coverslips. Coverslips were removed and immersed (10 min; −20° C.) in methanol:acetone (1:1) for cell fixation. NIH-3T3 cells were rehydrated (PBS (pH7.4); 30 min; 25° C.) and blocked (2 hr; 25° C.) using PBS (pH7.2) containing rat anti-mouse CD16/CD32 (1%), purified rat IgG (5%), FBS (10%) and Tween-20 (0.1%). Samples were washed (1 min) in PBS (pH7.2) containing BSA (1%) and Tween-20 (0.1%). Fixed cells were then incubated in medium containing 10 μg/ml 2F5 mAb, followed by extensive washing (2×150 mls; 10 min each; 1×150 mls; overnight) and bound Ab was visualized with goat anti-human IgG-FITC. Images were acquired using a Zeiss Axiovert 200M confocal immunofluorescence microscope (200× magnification, 50 ms exposure).

Results

The 2F5 Epitope is Expressed in a Mouse Cell Line.

Since 2F5 mAb reacts with self-antigens (Haynes et al, Science 308:1906-1908 (2005)) that are expressed in both mice and humans (Verkoczy et al, Proc. Natl. Acad. Sci. USA 107:181-186 (2010)) and FIG. 1A), an MPER tetramer reagent (GGGQQEKNEQELLELDKWASLWN) was used to test whether mechanisms of B-cell tolerance removed developing B cells that express 2F5-like Ab in BL/6 mice.

The B-cell tetramer reagents used in these studies have been previously described (Verkoczy et al, PLoS One 4:37215 (2009)) and consist of linear HIV-1 Env peptides synthesized with biotin, and tetramerized with streptavidin covalently linked to the allophycocyanin (APC) (Verkoczy et al, PLoS One 4:37215 (2009)). Similar tetramer reagents have been used to identify and isolate B lymphocytes that express receptors specific for HIV-1 Env antigens including the V3 loop of gp120 and the immunodominant region of gp41. The specificity of these B-cell tetramers has been demonstrated by surface plasmon resonance (SPR), reactivity to mAb-coated beads, and competitive inhibition (Verkoczy et al, PLoS One 4:37215 (2009)). Significantly, both 120- and gp41-specific human B cells can be enriched and isolated by tetramer-binding.

MPER Tetramer Binding to B Cells is Specific.

To identify B cells specific for the gp41 2F5 epitope, a biotinylated MPER polypeptide encompassing the 2F5 epitope was generated and tetramerized with streptavidin-APC. This MPER tetramer was bound only by human and mouse mAb specific for the 2F5 epitope of gp41 as determined by SPR and reactivity to mAb-coated beads (FIG. 8; Verkoczy et al, PLoS One 4:37215 (2009)), MPER tetramer binding to irrelevant mAbs and scrambled MPER tetramer was not observed (FIG. 8; Verkoczy et al, PLoS One 4:37215 (2009)).

As expected, MPER-tetramer binding to 13H11 cells, a 2F5-epitope reactive hybridoma line (Alam et al, J. Virol. 82:115-125 (2008)), was highly specific (FIGS. 1B, 1C). Approximately 60; % of 13H11 cells were labeled by APC-conjugated. MPER tetramer whereas APC-conjugated empty (no peptide) or irrelevant (R4A) tetramers labeled ≤20% of 13H11 cells (FIGS. 1B, 1C). Labeling of the parental fusion line, P3, by MPER- or control tetramers was even lower (≈5%) (FIG. 1B). To ensure further the specificity of MPER-tetramer binding, 13H11 cells were incubated with either unlabeled homologous or irrelevant tetramer or peptide (0.6 to 20-fold molar excess) and subsequently exposed to APC-conjugated MPER-tetramer (representative histograms, FIG. 8). Homologous peptide and unlabeled tetramer comparably reduced both the frequency and intensity of labeled 13H11 cells in a dose-dependent manner to background levels (FIGS. 1B, 1C). In contrast, pre-incubation with heterologous peptide or tetramer resulted in little (≤10%) to no reduction of MPER-tetramer labeling (FIGS. 1B, 1C).

To ensure that MPER-tetramer binding to mouse lymphocytes was equally specific, BL/6 BM cells (≈2×10⁶) were incubated in ice-cold medium or medium containing a 10-fold molar excess of unlabeled MPER peptide, the cells were washed and exposed to APC-conjugated MPER tetramer (125 ng/10⁶ cells). Subsequently the BM cells were reacted with B220 mAb to identify B-lineage cells. Whole BM cell populations contained a small (≤0.2%), but reproducible, population of MPER-tetramer⁺ B220⁺ cells; in those BM samples pre-incubated with soluble, homologous peptide, the frequency of MPER-tetramer⁺ cells were reduced by ≥80% (FIG. 1D). It was concluded that the substantial majority of B cells labeled by MPER-tetramer specifically bound the MPER-peptide, and that the MPER-tetramer identifies antigen-specific B-cell populations (FIG. 1D).

HIV MPER-reactive B Cells are Lost During the Transitional Stage of B-cell Development.

The developmental impairments of B cells in 2F5 VH-KI mice is consistent with the hypothesis that B cells recognizing some HIV gp41 MPER epitopes are removed by the mechanisms of self-tolerance (Verkoczy et al, Proc. Natl. Acad. Sci. USA 107:181-186 (2010)). To determine whether MPER-reactive B cells expressing endogenous Ig rearrangements might also be lost to tolerance mechanisms, the frequencies of MPER-tetramer binding in specific B-cell compartments of the BM and spleen were determined. These BL/6 BM and spleen cells were labeled with control and MPER tetramers along with mAbs that define specific subsets of B cells (FIG. 9) (Ueda et al, J. Immunol. 178:3593-3601 (2007)).

Figure 2:
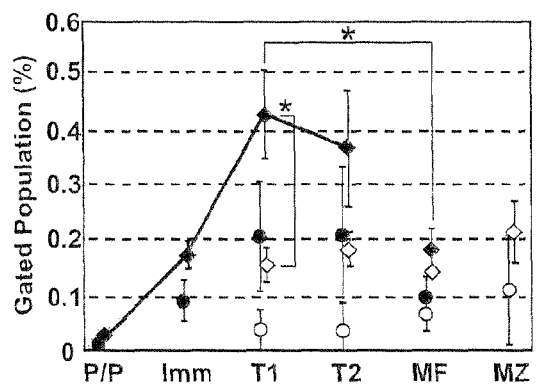
FIG. 2. BM transitional compartments contain MPER-tetramer binding B cells that are absent in peripheral B-cell compartments. BL/6 BM and spleen cells were harvested for flow cytometry. Cells (10$^6$) were labeled with 125 ng of MPER-APC (♦) or R4A-APC (●) tetramer. Cells were washed and labeled with mAb to B220, IgM, IgD, CD23 and CD21. Specific B-cell compartments of the BM (closed) and spleen (open) were identified (Ueda et al, J. Immunol. 178: 3593-3601 (2007)). Unlabeled control and empty tetramer (shaded gray area) samples were acquired to determine the maximum background signal. Data presented as the average and S.E.M. of the percent (%) of tetramer$^+$ cells within each B-cell compartment. Each group contained multiple mice (♦; n≥10 BM & Spl, ●; n=4 BM & Spl for R4A) compiled over 2-3 independent experiment. Significant differences (*; p≤0.05) between groups were determined by (two-tailed) Student's t-test.

B220$^{lo}$Ig$^{neg}$ B cells from BM (pro/preB and plasmablasts/-cytes) do not exhibit significant MPER-tetramer binding, whereas immature (~0.2%) and transitional (T) 1 and -2 (~0.4%) BM B cells were labeled by MPER-tetramer at low, but significant frequencies (FIG. 2). Significantly, splenic T1 and T2 B cells that were otherwise phenotypically similar to their BM counterparts, exhibited lower frequencies of MPER-tetramer labeling (p<0.05) that were indistinguishable from that of empty-tetramer controls (FIG. 2). Reactivity with the MPER-tetramer was not a general property of BM B cells as mature, recirculating, B cells present in the BM exhibited a low (~0.2%) frequency of MPER-binding cells (FIG. 2).

In the spleen, the frequencies of mature follicular (MF) and marginal zone (MZ) B cells that bound MPER-tetramer (~0.2%) were not significantly different (p≥0.20) from the frequencies of cells labeled by empty tetramer (FIG. 2), suggesting that mature MPER-reactive B cells are rare.

Taken together, these data are consistent with the generation of HIV-1 MPER-reactive B cells and their subsequent loss during the T1 and T2 stages of B-cell development in the BM. Indeed, this period of development known to be a major checkpoint of central B-cell tolerance (Melchers and Rolink, Curr. Top Microbiol. Immunol. 305:1-23 (2006)). It is believed that these experiments constitute the first demonstration of developmentally regulated reductions in the numbers of antigen-specific B cells in normal mice.

In vitro B-cell Culture System Rescues 2F5 VH-KI Immature and Transitional B-cell Development.

B-cell development in 2F5 VH-KI mice is blocked in the BM resulting in significantly reduced numbers of immature, transitional and mature B cells (Verkoczy et al, Proc. Natl. Acad. Sci. USA 107:181-186 (2010)). Earlier, stomal cell-independent, B-cell cultures that generate substantial numbers of IgM$^+$ B cells were developed and characterized, including those normally lost to immunological tolerance in the BM (Holl et al, J. Immunol. Methods 354:53-67 (2010)). This method allows the development of "forbidden", autoreactive B cells (e.g., DNA-specific 3H9 HC-KI) in vitro and their transfer and persistence into RAG1 deficient recipients (Holl et al, J. Immunol. Methods 354:53-67 (2010)).

Figure 3:
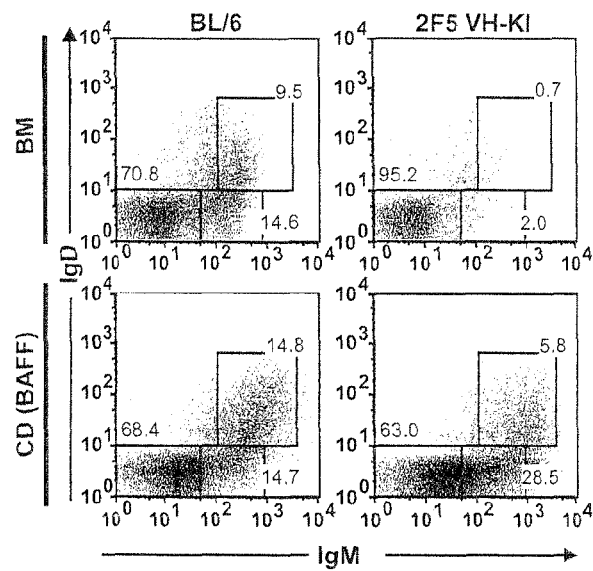
FIG. 3. In vitro culture of 2F5 VH-KI BM rescues development of transitional B cells that were absent in vivo. Non-adherent BL/6 (left) and 2F5 VH-KI (right) BM cells (top) were cultured with 10 ng/ml IL-7 followed by culture with 20 ng/ml BAFF (B cell activating factor belonging to the TNF family) (bottom). Cells were labeled with mAbs to B220, IgM, IgD, CD23, CD21 and CD93 to identify B-cell subsets. FACS diagrams were pre-gated on live, single B220$^+$CD93$^+$ cells using FlowJo software. FACS plots are representative of multiple (n=3) independent experiments.

To determine whether this in vitro recovery might allow the rescue of 2F5 VH-KI immature and transitional B-cell development, non-adherent BM cells from 2F5 VH-KI mice (Verkoczy et al, Proc. Natl. Acad. Sci. USA 107:181-186 (2010)) were cultured and their capacity to support B-cell development in vitro was characterized. As expected (Verkoczy et al, Proc. Natl. Acad. Sci. USA 107:181-186 (2010)), the BM of 2F5 VH-KI mice contains significantly (p<0.01) reduced numbers of immature and T1 B cells [~10% of BL/6 controls (FIG. 3)]; nonetheless, following the culture of 2F5 VH-KI BM in IL-7 and BAFF (Holl et al, J. Immunol. Methods 354:53-67 (2010)), substantial numbers (≈35% of BL/6 controls) of immature and T1/T2 2F5 VH-KI B cells were recovered (FIG. 3). Frequencies of immature and transitional 2F5 VH-KI CD B cells were much greater (~10-fold) than the corresponding 2F5 VH-KI compartments in BM (FIG. 3, right panels), demonstrating that this culture system is permissive for the development of 2F5 VH-KI B-cell compartments that are normally lost during development (Verkoczy et al, Proc. Natl. Acad. Sci. USA 107:181-186 (2010)).

In vitro Culture of BL/6 BM Supports the Development of HIV-1 MPER-reactive B Cells.

The specificity of B lymphocytes that can generate Ab specific for the 2F5 MPER epitope has yet to be characterized. As the CD B cells are grown in vitro, absent the normal BM micro-environment that supports tolerization (Sandel et al, J. Immunol. 166:5935-5944 (2001), Sandel and Monroe Immunity 10:289-299 (1999)), a test was made to determine if this culture system supported the development of MPER-reactive B cells from BL/6 mouse BM. CD B cells were labeled with control (empty), R4A- or MPER-tetramers (FIGS. 1B-1C) along with B220, IgM and IgD mAb. By this method, MPER-specific B cells (0.2-0.4% of T1 or T2 compartments) were identified as tetramer positive cells (FIG. 4A).

Figure 4:
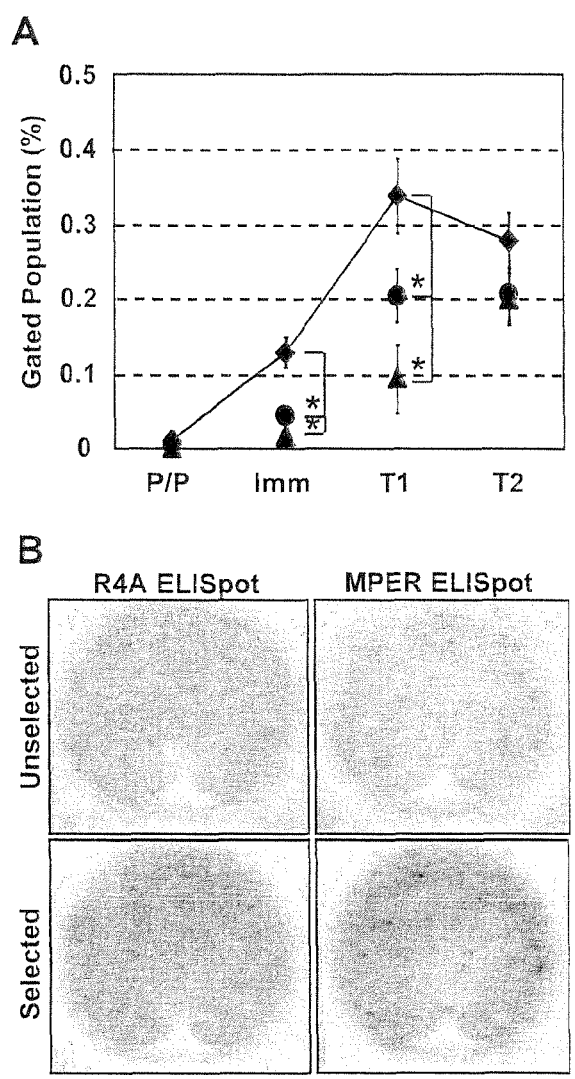
FIGS. 4A and 4B. In vitro culture of BL/6 BM generates MPER-reactive B cells. BM cells were cultured using a standard method to generate Ig$^+$ B cells (Holl et al, J. Immunol. Methods 354:53-67 (2010)).

B220$^{lo}$Ig$^{neg}$ cells from these cultures do not exhibit significant MPER-tetramer binding, whereas immature (~0.15%) and T1/T2 (~0.35%) CD B cells were labeled by MPER-tetramer at low, but significant frequencies (FIG. 4). Few immature and T1 CD B cells bound the empty-tetramer (≤0.1%), suggesting that the majority (~75%) of labeling by MPER- and R4A-tetramers was peptide-specific (FIG. 4A). For T1 and T2 CD B cells, the frequencies of MPER-reactive cells are not significantly different (p=0.10 and 0.40, respectively) than that observed in the transitional compartments of BM (FIG. 2). These data demonstrate that MPER-reactive B cells are efficiently generated from BL/6 BM using this culture system, thereby opening an avenue of investigation into the repertoire of B lymphocytes specific for the 2F5 MPER epitope.

It was confirmed that in vitro cultures of BL/6 BM cells supported the development of MPER-specific CD B cells using the ELISpot method. CD B cells differentiate into antibody forming cells (AFC) after stimulation with BAFF and LPS (Holl et al, J. Immunol. Methods 354:53-67 (2010)). The frequency of R4A- and MPER-antigen specific AFC was determined using biotinylated-peptide reverse ELISpot assays (Verkoczy et al, PLoS One 4:37215 (2009)). Both R4A-and MPER-specific AFC were present (~0.1-0.4%) in LPS/BAFF-activated CD B cells (FIG. 4B, unselected), data that are congruent with the frequency of MPER-specific B cells obtained via tetramer labeling experiments (FIG. 4A). FACS enrichment of MPER-tetramer$^+$ CD B cells substantially increased (~12 fold) the frequency of MPER-reactive AFC (by ELISpot) (FIG. 4B, selected). By comparison, selection of MPER-tetramer$^+$ CD B cells showed little (<2-fold increase) change in the frequency of R4A-reactive AFC (by ELISpot) (FIG. 4B, selected). These data demonstrate that tetramer labeling of B-cell compartments can be used to selectively enrich for antigen-specific cells as demonstrated by previous experiments (Scheid et al, Nature 458:636-640 (2009)).

RAG-1$^{-/-}$ Mice Reconstituted with CD B Cells, but not LN B Cells, Exhibit High Titers of Serum Autoantibody CD cells reconstitute the peripheral lymphoid tissues of RAG-1$^{-/-}$ mice (Holl et al, J. Immunol. Methods 354:53-67 (2010)) where they result in persistent, elevated levels of serum autoantibody (Holl et al, J. Immunol. Methods 354:53-67 (2010)) and MPER-reactive cells (FIG. 4). Mature, "self-tolerant" B cells isolated from BL/6 LNs did not form autoantibody upon transfer to RAG-1$^{-/-}$ mice, indicating that CD-RAG mice provided an experimental model to study B-cell populations that are normally excluded from the mature repertoire.

Peripheral lymphoid tissues of RAG-1$^{-/-}$ mice were repopulated with lymphocytes after transfer of either CD or LN cells (FIG. 5A). Similar to CD-RAG mice, the frequency of splenic MZ-like (IgM$^{hi}$IgD$^{lo}$CD21$^{hi}$) B cells was elevated in LN-RAG mice when compared to BL/6 controls (FIG. 5A). CD-RAG mice contained comparable frequencies of mature follicular)(IgM$^{lo}$IgD$^{hi}$CD21$^{lo}$) and MZ-like LN B cells to that of BL/6 mice; however, LN-RAG mice contained elevated (~3 to 5-fold) frequencies of MZ-like LN B cells compared to either BL/6 or CD-RAG mice (FIG. 5A). A population of B220$^{hi}$IgM$^{neg}$IgD$^{neg}$ B cells was observed in the spleen and LNs of both CD- and LN-RAG mice (FIG. 5A), a phenotype consistent with B cells that have undergone class-switch recombination. These data indicated that LN or CD cells were equivalent in their capacity to reconstitute RAG-1$^{-/-}$ mice.

DNA autoantibody was detected in the serum (1:160 dilution) of BL/6, CD- and LN-RAG mice using *Crithidia luciliae* direct immunofluorescence assay (Gilkeson et al, J. Clin. Invest. 95:1398-1402 (1995)) by dividing the observed binding into strong (++), weak (+) and no (−) reactivity (representative images for each category in FIG. 5B). BL/6 sera samples contained only weak (1/5) or no (4/5) reactivity to DNA (FIG. 5C). In contrast, CD-RAG sera samples contained mostly (4/5) strong reactivity to DNA (FIG. 5C), while most LN-RAG samples (3/5) showed no reactivity to DNA (FIG. 5C). To ensure that differences in serum DNA Ab was not the result of unequal IgG reconstitution, a direct comparison was made of the ability of CD and LN B cells to reconstitute serum IgG using ELISA (FIG. 5C). It was observed that both CD- and LN-RAG mouse serum contained similar (~1.5 mg/ml) amounts of IgG to that of BL/6 controls (FIG. 5C). These data support the conclusion that the B-cell repertoire formed in vitro is qualitatively different from the mature, peripheral B-cell repertoire of BL/6 mice, indicating that the CD-RAG animal model can be used to study B-cell populations that are normally excluded from the mature repertoire.

CD-RAG Mice Mount Robust Germinal Center Responses after Immunization with MPER Antigen CD B cells contained MPER-specific populations (FIGS. 3, 4) and were able to reconstitute lymphocyte-deficient mice with a unique repertoire of B cells (Holl et al, J. Immunol. Methods 354:53-67 (2010); FIG. 5); interestingly, it was determined that CD-RAG mice could respond to immunization with MPER peptide antigen precipitated in aluminum sulfate (alum). The spleen and mesenteric LNs (MLN) of control and immunized mice (d16 post-immunization) were harvested and the frequency of germinal center (GC) B cells ($B220^{hi}GL-7^{hi}$) within the total $B220^+$ population (FIGS. 6A, 6B) was determined for each tissue. Additionally, the presence of GC structures was confirmed by histological analysis of spleen and MLN samples (representative examples in FIGS. 6C, 6D).

In BL/6 mice, immunization with MPER antigen did not significantly increase (1° p=0.80; 2° p=0.52) the frequency of MLN GC B cells when compared to naïve animals (FIG. 6A). Histological analysis (FIG. 6C) confirmed that BL/6 mice did not form robust splenic GC responses after MPER antigen immunization as determined by small increases (1° p=0.04; 2° p=0.10) in the frequency of GC B cells by FACS (FIG. 6B). The observations that BL/6 mice do not elicit robust GC responses upon MPER-peptide immunization are correlated with the loss in frequency of MPER-specific mature B cells demonstrated previously (FIG. 2).

In contrast, immunization of CD-RAG mice with MPER antigen significantly increased (1° p=0.01; 2° p=0.05) the frequency of MLN GC B cells (FIG. 6A) and initiated robust splenic GC reactions (FIG. 6B). Histological analysis of spleen samples from these immunized CD-RAG mice confirmed that $GL-7^{hi}$ B cells were organized into GC structures (FIGS. 6C, 6D). Compared to BL/6 controls, CD-RAG mice contained significantly elevated (MLN: 1° p<0.01; 2° p=0.01 and Spl: 1° p=0.01; 2° p=0.05) frequencies of GC B cells after each immunization with MPER antigen (FIGS. 6A, 6B). These data demonstrate that CD-RAG mice mount robust GC responses to MPER antigen immunization and these observations are correlated with the recovery of MPER-reactive B cells using the culture system.

Immunized CD-RAG Mice Contain Elevated MPER-reactive IgG Ab

Figure 6:
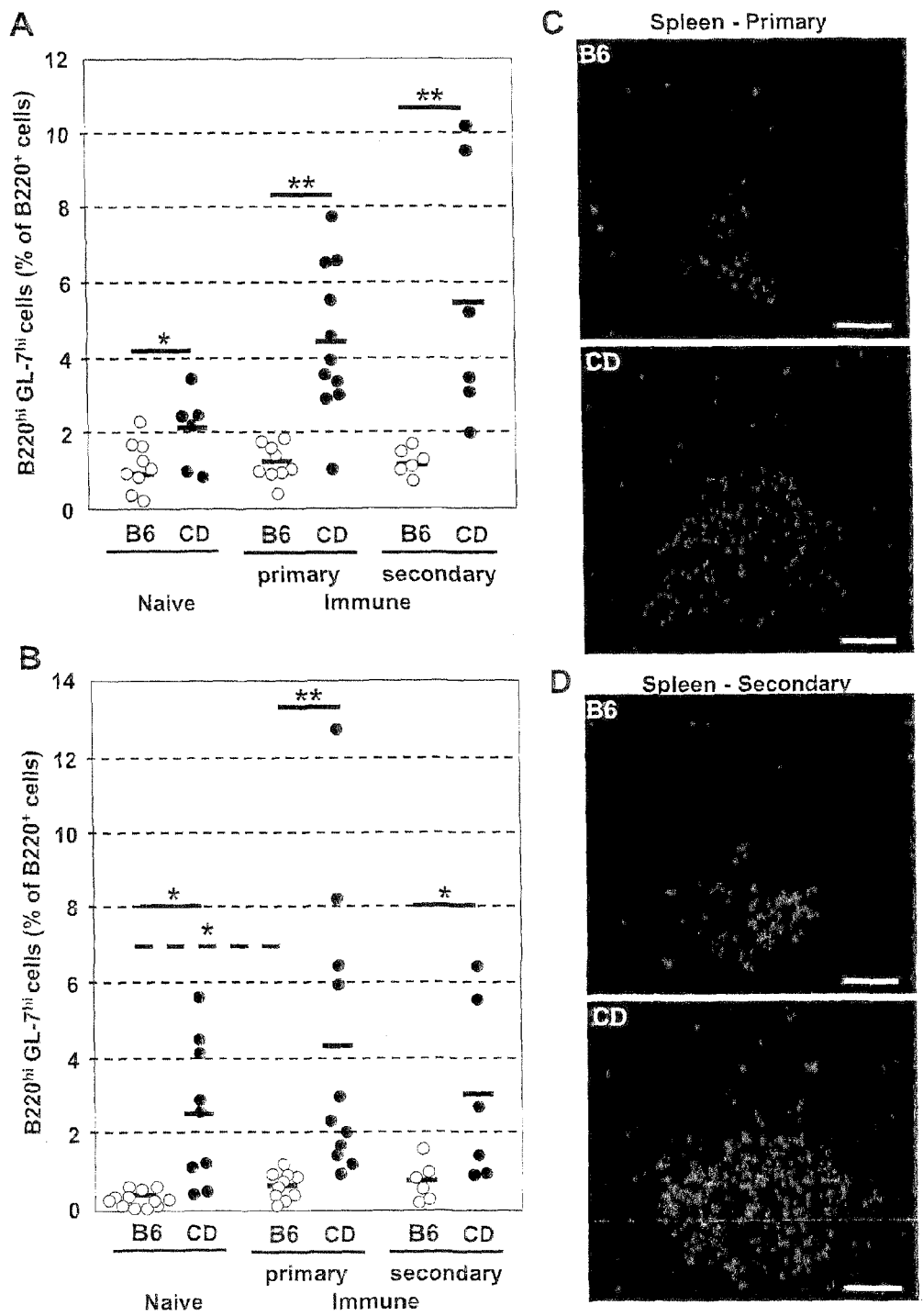
FIGS. 6A-6D. CD-RAG mice form robust GC responses after immunization with MPER peptide. BL/6 (○) and CD-RAG (●) mice were immunized (ip) with 10 μg DP178-Q16L (MPER) peptide in alum.

Historically, 2F5-like gp41 MPER-specific serum Ab is poorly elicited after immunization with HIV-1 antigen (Coeffier et al, Vaccine 19:684-693 (2000), Derby et al, J. Virol. 80:8745-8762 (2006), Eckhart et al, J. Gen. Virol. 77(Pt9): 2001-2008 (1996), Ferrantelli and Ruprecht, Curr. Opin. Immunol. 14:495-502 (2002)). CD B cells reconstituted peripheral lymphoid tissues, organized into follicles and formed GC reactions upon MPER antigen immunization (FIGS. 5, 6). Moreover, CD-RAG mice were capable of forming antigen-specific IgG to NP-CGG and this response was compared to the generation of gp41 MPER-reactive Ab after immunization. The serum of naïve and antigen-immunized mice was collected and antigen-specific serum Ab was quantified by ELISA containing standard curves.

Figure 7:
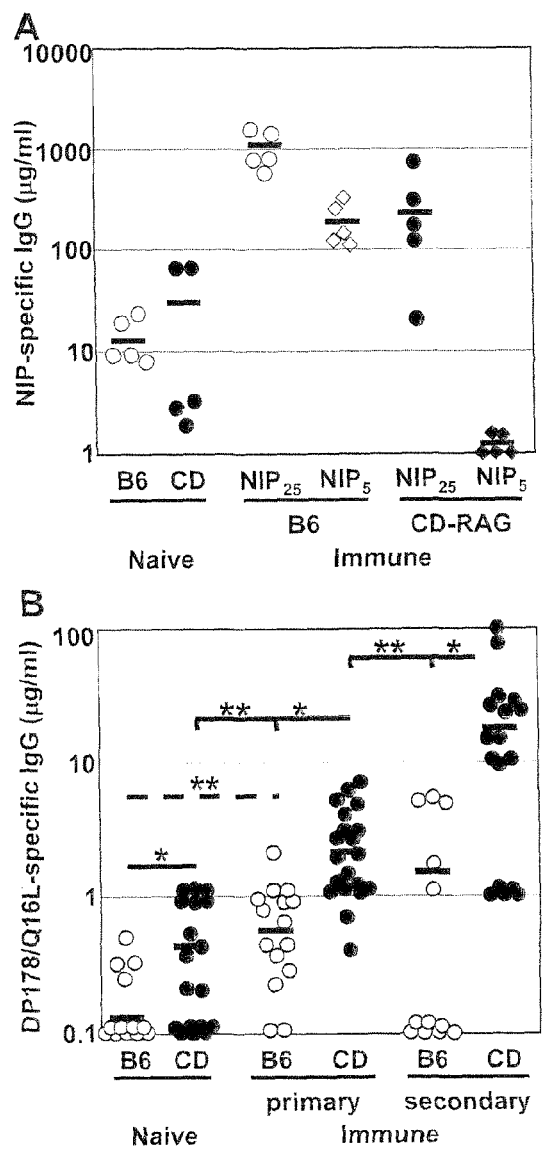
FIGS. 7A and 7B. MPER-specific serum IgG responses are enhanced in CD-RAG mice, but not in BL/6 mice, after immunization.

Immunization of BL/6 and CD-RAG mice with NP-CGG/alum elicited a large increase (~100- and 30-fold, respectively) in NIP-specific serum IgG Ab compared to naïve animals (FIG. 7A). NIP-specific serum IgG of CD-RAG mice was ~3-fold less than elicited in BL/6 mice (FIG. 7A), indicating that CD-RAG animals are capable of mounting a B-cell response to antigen immunization that is proportional to their level of cellular reconstitution.

B cells modify their B-cell receptor in the GC reaction resulting in the preferential expansion of high affinity clones, a process termed affinity maturation (AM) (Jacob et al, J. Exp. Med 173:1165-1175 (1991), Jacob et al, Nature 354:389-392 (1991)); while low affinity clones are eliminated by apoptosis (Rajewsky, Nature 381:751-758 (1996)). Affinity maturation of serum IgG antibody was measured in NP-CGG immunized mice by determining serum IgG reactivity to $NIP_S$-BSA. While serum from immunized BL/6 mice contained $NIP_5$-reactive IgG (~30% of $NIP_{25}$), serum from immunized CD-RAG mice showed no evidence for AM (FIG. 7A).

Prior to immunization, sera from many naive animals did not contain a detectable amount of MPER-reactive IgG Ab; however, some naïve BL/6 mice (4/13) and CD-RAG mice (11/18) contained MPER-specific IgG (~0.5 µg/ml) that was near the limit of detection by ELISA (FIG. 7B). If these low amounts of MPER Ab represent real binding, these data are consistent with CD-RAG mice containing higher levels of serum autoantibody (Holl et al, J. Immunol. Methods 354:53-67 (2010)), a potential source of MPER-reactive Ab. After primary immunization of BL/6 mice with MPER peptide, a significant increase (p<0.01) in MPER-specific serum IgG be detected; however, the average amount of Ab was low (~0.7 µg/ml) (FIG. 7B). After secondary challenge of BL/6 mice with MPER peptide, the level of antigen-specific IgG did not significantly increase (~2-fold) over primary challenge (FIG. 7B), indicating the humoral memory to this MPER peptide was not formed.

In contrast, primary immunization of CD-RAG mice resulted in significantly (p<0.01) more (~3 µg/ml) MPER-specific IgG serum Ab than was formed in immunized BL/6 mice (FIG. 7B). CD-RAG mice that received secondary immunization significantly (p<0.01) increased (~10-fold) the amount of MPER-specific IgG (~25 µg/ml) over primary challenge (FIG. 7B). This robust expansion of MPER-specific IgG suggests that CD-RAG mice had formed humoral memory to the MPER peptide during the initial immunization. These data demonstrate that the humoral immune response to this HIV-1 gp41 MPER peptide antigen can be restored in mice when the constraints of B-cell tolerance have been relaxed.

In summary, the inability to mount robust B-cell responses to some MPER antigens appears to be phylogenetically conserved from rodents to humans (Graham, Annu. Rev. Med. 53:207-221 (2002), Letvin et al, Annu. Rev. Immunol. 20:73-99 (2002)). Recent work has characterized the Ab response to HIV gp41 in patients whose serum contains moderate-to-high virus neutralizing activity (Pietzsch et al, J. Virol. 84:5032-5042 (2010)). Interestingly, these mAbs were not able to compete away the binding of 2F5 and 4E10 Ab for their respective MPER epitopes (Pietzsch et al, J. Virol. 84:5032-5042 (2010)), illustrating the rarity of humoral responses to the MPER region of the gp41 envelope antigen. Haynes et al. has reported that these rare Abs (2F5 and 4E10) are polyreactive, cross-react with highly conserved self antigens and went on to discuss that tolerance mechanisms may limit MPER Ab production in vivo (Haynes et al, Science 308: 1906-1908 (2005). This "tolerance hypothesis" represents an explanation for this state of non-responsiveness to gp41 MPER antigen(s) (Haynes et al, Hum. Antibodies 14:59-67 (2005)). The study described above provides a direct test of the notion that MPER peptides mimic self antigens and that B cells reactive to these epitopes are tolerized in the BM transitional compartments.

The tetramer studies demonstrate the loss of MPER antigen-reactive cells in the T1/T2 B-cell compartments of the spleen, suggesting removal by central tolerance mechanisms (e.g. deletion or receptor editing). A critical question is if B-cell compartments that are enriched for self-reactive lymphocytes contain elevated frequencies of HIV-1 MPER-reactive cells. The marginal zone (MZ) B-cell compartment is a natural reservoir of autoreactive B cells in mice (reviewed in Lopes-Carvalho and Kearney, Immunol. Rev. 197:192-205 (2004)). The data demonstrate that the MZ B-cell compartment was not enriched for MPER-tetramer+ B cells (FIG. 2), supporting the conclusion that MPER-reactive cells are efficiently deleted or undergo receptor editing as previously demonstrated (Verkoczy et al, Proc. Natl. Acad. Sci. USA 107:181-186 (2010)), Furthermore, the data indicate that B cells reactive to this linear peptide epitope of the MPER can be recovered in mice that contain frequent autoreactive B cells.

In humans, the frequency of autoreactive Ab declines with increasing developmental maturity by virtue of apoptotic loss and receptor editing (Wardemann et al, J. Exp. Med. 200:191-199 (2004), Wardemann et al, Science 301:1374-1377 (2003)), even when cells were recovered from peripheral sites (Meffre et al, J. Exp. Med. 199:145-150 (2004), Tsuiji et al, J. Exp. Med. 203:393-400 (2006)). These declining frequencies of self-reactive B cells demonstrate the mitigating effects of tolerizing processes (Wardemann et al, J. Exp. Med. 200:191-199 (2004), Wardemann et al, Science 301:1374-1377 (2003)) and suggest that the frequency of self- and MPER-reactive human B cells will sequentially decrease as B cells mature. It is critical to study patients to understand the mechanisms of MPER Ab generation when they occur. Do donors that can readily make 2F5- and 4E10-like Abs have a predisposition to autoimmune diseases? Alternatively, it is possible that these donors contain mutation(s) within the self-antigen(s) that 2F5 and 4E10 recognizes, effectively removing the constraints of B-cell tolerance on this Ab repertoire.

Previous studies of MPER-reactive Ab have yielded their physical structure, neutralizing capacity and antigen reactivity. The 2F5 and 4E10 Ab contain long, hydrophobic complementarity-determining region-3 (CDR3) structures that are similar to many human Ab shown to be deleted in the BM (Meffre et al, J. Exp. Med. 199:145-150 (2004)). In addition to the MPER region of HIV gp41, 2F5 and 4E10 Abs show significant affinity to highly conserved self-antigens, such as cardiolipin and phosphatidylserine (PS). Previously, investigators have shown that anti-PS-reactive B-cell clones are deleted in BM due to receptor editing (Li et al, Immunity 18:185-192 (2003)). Combined, these data indicate that a narrow balance must be found between measures required to elicit an appropriate anti-MPER humoral response and the potential to elicit equally harmful autoimmunity.

It has been suggested that the lipid reactivity of 2F5 and 4E10 may subject these Abs to control by tolerance mechanisms (Verkoczy et al, Proc. Natl. Acad. Sci. USA 107:181-186 (2010)). These studies suggest that it is the 2F5 MPER determinant that is critical for induction of tolerance control. This notion is supported by observations that many residual peripheral B cells that escape central clonal deletion in 2F5 VH-KI mice have lost MPER reactivity but retain their lipid reactivity.

Normally, the GC reaction must balance AM and the elimination of newly formed self-reactive B cells that arise via somatic hypermutation (Han et al, J. Exp. Med. 182:1635-1644 (1995)). Therefore, it is somewhat surprising that both 2F5 and 4E10 exhibit the hallmarks of maturing through the GC reaction (AM) yet retain significant affinity to phylogenetically conserved self-antigens. It is possible that for B cells to acquire HIV-neutralizing capacity, a circuitous path of mutation and antigen-mediated selection may be required to avoid the induction of B-cell tolerance mechanisms. It would appear that in mice the mature peripheral B-cell pool is purged of MPER-reactive cells that would be recruited to the GC reaction upon immunization. The B-cell transfer model may work simply by increasing the frequency of cells that are available to initiate this difficult path to protection.

EXAMPLE 2

General Protocol for Generating Hybridomas from CD 2F5 $V_H^{+/+} \times V_L^{+/+}$ KI B Cells Step 1: Tissue preparation. 8 week old female 2F5 "full knock-in" (2F5 $V_H^{+/+} \times V_L^{+/+}$ KI) or wild-type (WT) C57BL/6 littermate control mice were euthanized, bone marrow (BM) was collected by repeated flushing of hind leg long bones with cold IMDM media, single cell BM suspensions were prepared by repeated pipetting, and viability was assessed by trypan blue exclusion staining.

Step 2: Generation of culture-derived B cells. Culture-derived (CD) WT or 2F5 $V_H^{+/+} \times V_L^{+/+}$ KI B cells were generated based on methodologies outlined in Holl et al (J. Immunol. Methods. 354:53-67 (2010)). Briefly, single cell BM suspensions from WT or 2F5 $V_H^{+/+} \times V_L^{+/+}$ KI mice made in step 1 were incubated briefly (15 min at 37° C.) in 10 cm culture dishes to allow for cells to adhere. Non-adherent cells were then recovered by centrifugation, depleted of erythrocytes by ACK lysis, washed, transferred into T-75 flasks, and incubated at $7.5 \times 10^5$ for 4 days in IMDM media supplemented with recombinant mouse IL-7 (10 ng/ml), followed by washing, and re-plating in IMDM media supplemented with BAFF (20-100 ng/ml) for an additional 3-4 days.

Step 3: Flow Cytometry. Aliquots of WT and $V_H^{+/+} \times V_L^{+/+}$ 2F5 KI BM B cells (either prior to culture or at different stages of culture in the CD system i.e. in BAFF and/or IL-7) were phenotypically assessed by flow cytometry using standard staining methods. Briefly, $10^6$ cells were suspended in FACS Buffer containing 1×PBS (pH7.2), 3% FBS (Sigma) and 0.01% Sodium Azide, and B cells were stained with the following combination of fluorochrome-labeled mAbs: PacificBlue-conjugated anti-B220 (clone RA3-6B2), PEcy7-labeled anti-mouse IgM (clone 15F9), and FITC-conjugated anti-mouse IgD (clone 11-26). Propidium iodide (PI) was used to exclude dead cells from samples. All FACS analysis was performed using a BD LSRII cytometer and analyzed using FloJo software.

Step 4: Electrofusions. CD 2F5 $V_H^+ \times V_L^{+/+}$ KI B cells (after sequential culture in IL-7+BAFF as described in Step 92) were used to generate primary CD 2F5 $V_H^{+/+} \times V_L^{+/+}$ KI hybridoma cultures by electrofusion as follows: NS0-Bcl$_2$ myeloma partner cells and CD 2F5 $V_H^{+/+} \times V_L^{+/+}$ KI B cells were washed twice with an isoosmolar electrofusion buffer (Eppendorf), and fused at a 1:2 B cell:myeloma ratio using a PA-4000/PA-101 electrofusion apparatus with FE-20/800 electrode fusion chamber (Cyto Pulse Sciences, Inc.). Pre-fusion dielectrophoresis was performed with an alternating current voltage of 40V-60V at 1.4 MHz for 20 s. Cells were fused with a single square-wave direct current voltage of 525 V for 0.04 ms. Post-fusion dielectrophoresis was performed with an alternating current voltages of 50V-5V at 1.4 MHz for 30 s. After fusion, cells were harvested and distributed into 96 well plates (flat-bottom) at 1,000 B cells per well and incubated in culture medium supplemented with 100 µM hypoxanthine, 0.4 µM aminopterin, and 16 µM thymidine.

Step 5: Screening/cloning of hybridoma cultures. After 2 weeks in culture, hybridoma supernatants from Step 4 (and from wells with cell growth) were screened for neutralization, total Ig levels, and MPER reactivity. The ability to neutralize HIV-1 was assessed by the TZM-b1 pseudovirus assay using an HIV-1 strain, MN, which has been shown to be sensitive to bnAbs of both IgG and IgM isotypes. MPER reactivity assays were determined by ELISA using the MPER-specific peptide SP62, as previously described (Haynes et al, Hum. Antibodies 14:59-67 (2005), Alam et al, J. Virol. 82:115-125 (2008)). Total Ig levels were quantitated by sandwich ELISA using purified goat anti-mouse kappa+lambda and AP-conjugated goat anti-mouse IgM+IgG+IgA reagents (both from Southern Biotech) for capture and detection, respectively. Supernatants with detectable total Ig levels were also isotyped using a Milliplex mouse Ig isotyping immunoassay kit and a BioRad Luminex Bead Array Reader. All wells with cell growth (regardless of outcome under the various criteria listed above) were cloned by limiting dilution.

Figure 10A:
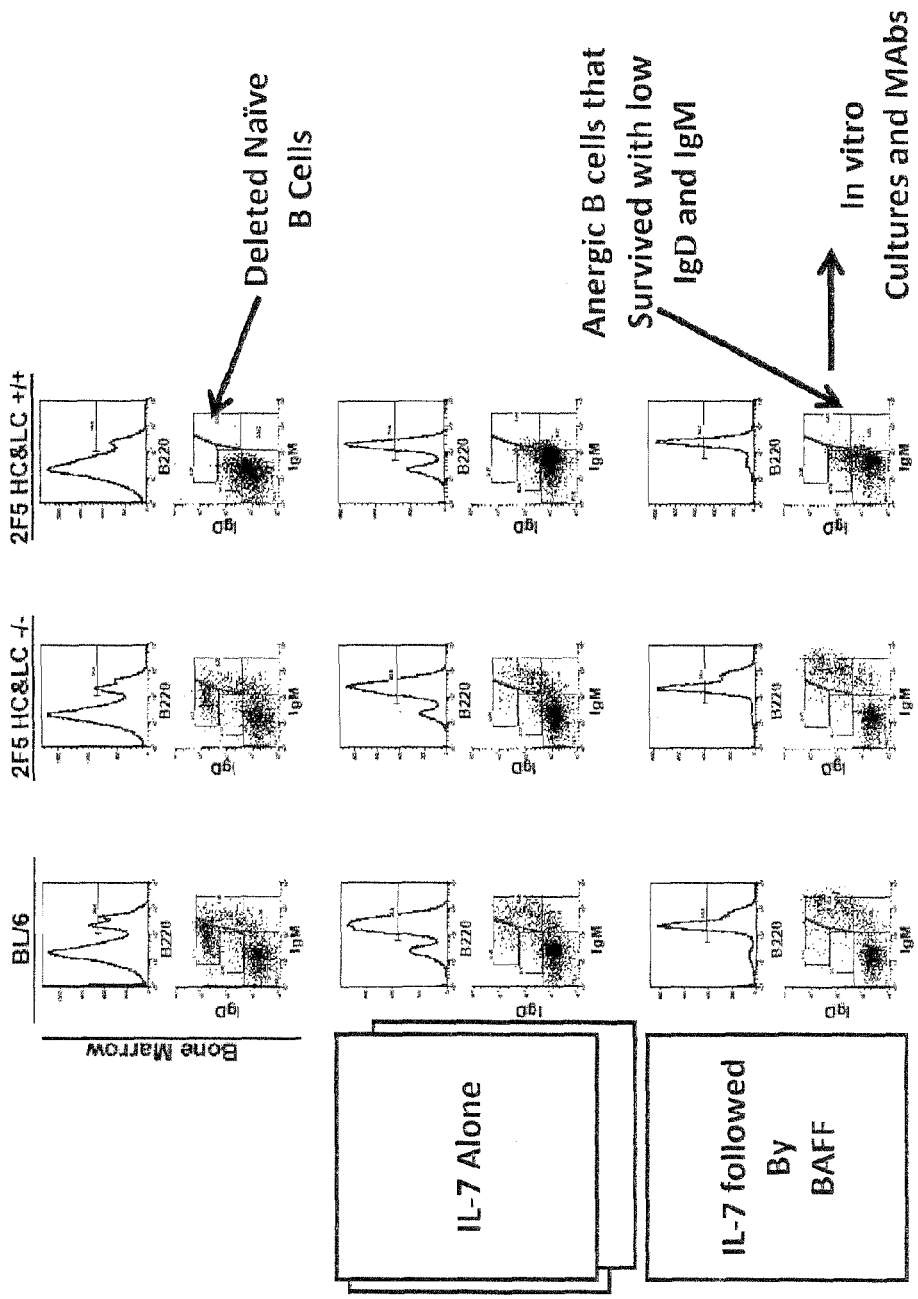

The results are shown in FIG. 10.

\* \* \*

All documents and other information sources cited above are hereby incorporated in their entirety by reference.

What is claimed is:

1. A method of inducing the production in a subject of broadly neutralizing antibodies against HIV-1 comprising administering to said subject an HIV-1 immunogen and an adjuvant comprising B-cell-activating factor of the tumor necrosis factor family (BAFF) and interleukin (IL)-7, wherein said HIV-1 immunogen is a membrane-proximal external region (MPER) antigen, or variant thereof.

2. The method according to claim 1 wherein said subject is a human subject.

3. The method according to claim 1 wherein said variant is a MPER epitope peptide with an L669S mutation that confers higher neutralization sensitivity to MPER monoclonal antibodies 2F5 and 4E10.

4. The method according to claim 1 wherein the HIV-1 immunogen is a transmitted founder HIV-1 Env, or fragment thereof.

5. The method according to claim 1 wherein said adjuvant is co-administered with said HIV-1 immunogen or is administered before administration of the immunogen.

6. The method according to claim 1 wherein BAFF and IL-7 are administered separately.

7. The method according to claim 1 wherein a DNA sequence encoding said adjuvant is administered under conditions such that said adjuvant is produced in vivo.

8. The method according to claim 1 wherein said HIV-1 immunogen is present in a liposome with BAFF or IL-7.

9. The method according to claim 1 wherein said liposome comprises POPC, POPE, DMPA, lysophosphorylcholine, phosphatidylserine or cholesterol.

10. The method according to claim 1 wherein a DNA sequence encoding sad HIV-1 immunogen is administered under conditions such that said immunogen is produced in vivo.

11. The method according to claim 1 wherein said method further comprises administering a squalene-based adjuvant, a TLR agonist, alum, Q521, or oligo CpGs in an oil emulsion.

\* \* \* \* \*